(12) United States Patent
Vacher et al.

(10) Patent No.: US 6,417,222 B1
(45) Date of Patent: Jul. 9, 2002

(54) [2-SUBSTITUTED-5-[3-THIENYL)-BENZYL]-2-([2-ISOPROPOXY-5-FLUORO]-PHENYOXY)-ETHYL]-AMINE DERIVATIVES, METHOD FOR THE PRODUCTION AND USE THEREOF AS MEDICAMENTS

(75) Inventors: Bernard Vacher; Stéphane Cuisiat, both of Castres; Wouter Koek, Viviers les Montagnes, all of (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/937,737
(22) PCT Filed: Mar. 29, 2000
(86) PCT No.: PCT/FR00/00775
§ 371 (c)(1), (2), (4) Date: Sep. 28, 2001
(87) PCT Pub. No.: WO00/58282
PCT Pub. Date: Oct. 5, 2000

(30) Foreign Application Priority Data

Mar. 29, 1999 (FR) .............................. 99 03875

(51) Int. Cl.[7] ................... C07D 333/08; A61K 31/381; A61P 25/00
(52) U.S. Cl. ......................... 514/438; 549/75
(58) Field of Search ............................. 549/75; 514/438

(56) References Cited

FOREIGN PATENT DOCUMENTS

FR 2 248 830 * 5/1975
WO 94/20466 * 9/1994
WO 2000032557 * 6/2000

OTHER PUBLICATIONS

Mewshaw, et al, 1997, Bioorg. Med. Chem. Lett., 8(3), 295–300.*

* cited by examiner

*Primary Examiner*—Floyd D. Higel
*Assistant Examiner*—Andrea D'Souza Small
(74) *Attorney, Agent, or Firm*—The Firm of Hueschen and Sage; G. Patrick Sage

(57) ABSTRACT

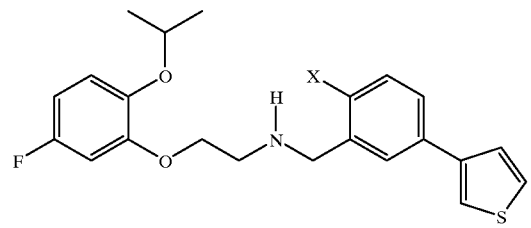

(1)

The present invention relates to novel [(2-substituted-5-[3-thienyl])-benzyl]-[2-([2-isopropoxy-5-fluoro]-phenoxy)-ethyl]-amine derivatives having formula (1) and the use thereof as medicaments, especially anti-psychotic medicaments.

6 Claims, No Drawings

[2-SUBSTITUTED-5-[3-THIENYL)-BENZYL]-2-([2-ISOPROPOXY-5-FLUORO]-PHENYOXY)-ETHYL]-AMINE DERIVATIVES, METHOD FOR THE PRODUCTION AND USE THEREOF AS MEDICAMENTS

This application is a 371 of PCT/FR00/00775 Mar. 29, 2000.

Dopamine is a neuromediator which participates in controlling motricity, cognitive functions and mood, and is involved in the compensation circuit. Five types of dopaminergic receptors have been cloned ($D_1-D_5$) and their levels of expression and cerebral distributions have been analyzed. Among these five types of receptor, at least two types have isoforms (Proc. Natl. Acad. Sci. USA 1998, 95, 7731). Although these five types of dopaminergic receptor are pharmacologically distinct, they have been grouped into 2 subfamilies: the $D_1$ subfamily, which comprises the $D_1$ and $D_5$ receptors, and the $D_2$ subfamily, which comprises the $D_2$, $D_3$ and $D_4$ receptors. It is possible to differentiate the pharmacological action of the $D_1$ and $D_2$ subfamilies, but it is generally difficult to differentiate the function of the various types within each subfamily.

A dysfunction of dopaminergic transmission is involved in the symptomatology of central nervous system disorders such as schizophrenic psychosis (Neuropsychopharmacol. 1988, 1, 179), certain neurodegenerative diseases such as, for example, Parkinson's disease (Neurodegenerative Diseases; Jolles, G.; Stutzmann, J. M.; Eds; Academic Press, 1994, Chap. 8), depression (J. Clin. Psychiatry, 1998, 59 (Suppl. 5), 60), the dependance on certain substances such as, for example, cocaine, tobacco or alcohol (Cell 1997, 90, 991; Nature 1997, 388, 586). Thus, for example, antagonists of central dopaminergic receptors of the $D_2$ type constitute a conventional and clinically effective approach in the treatment of the positive symptoms of schizophrenic psychosis. However, most of the compounds having such a mechanism of action also induce adverse side effects such as symptoms of Parkinson type (Pharmacotherapy 1996, 16, 160) and/or neuroendocrine disorders (Acta Psychiatr. Scand. 1989, 352, 24).

Mewshaw et al. (Bioorg. Med. Chem. Lett. 1998, 8, 295) have described phenoxyethylamines of formula:

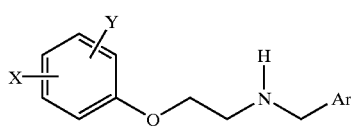

in which X represents a hydrogen atom, a hydroxyl group, an amino group or a methanesulfonamide group, Y represents a hydrogen atom or a halogen atom and Ar is a phenyl or 2-thienyl group, as being partial agonists of the receptor of the $D_2$ type.

Patents WO 98/08817, U.S. Pat. No. 5,760,070, WO 98/08843 and WO 98/08819 describe, respectively, 4-aminoethoxyindoles and 4-aminoethoxyindolones as being agonists of dopaminergic receptors of the $D_2$ type or inhibitors of the synthesis and release of dopamine.

Unangst et al. (J. Med. Chem. 1997, 40, 4026) have described aryloxyalkylamines of formula:

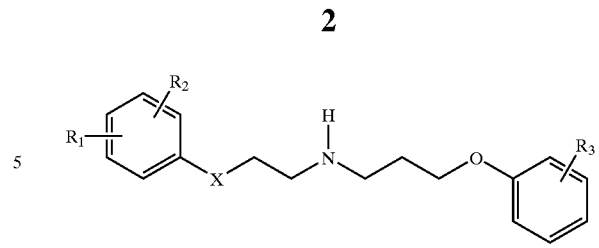

in which X represents a n oxygen or sulfur atom or a $CH_2$ group; $R_1$ is a hydrogen or chlorine atom, a hydroxyl or hydroxymethyl group, a nitro group or a hydroxy-carbonyl residue; $R_2$ and $R_3$ represent a hydrogen atom, a halogen atom or a methyl group. These compounds are active on the dopaminergic system, in particular on the receptors of the $D_4$ type, and are potentially useful in the treatment of schizophrenia.

Patent WO 97/23482 describes octahydropyrrolo[1,2-a]-pyrazines of formula:

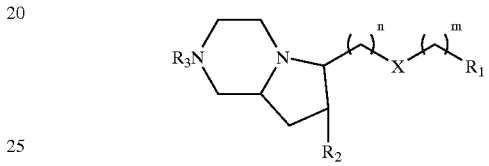

in which X represents, inter alia, an oxygen atom; m and n=0, 1, 2 and $R_1$ is an unsubstituted, heterocyclic or non-heterocyclic, polycyclic or non-polycyclic aromatic group. These compounds have affinity for the dopaminergic receptors, in particular for the receptors of the $D_4$ type.

Patents FR 2 702 211, JP 51 048 627, JP 51 052 146, DE 2 450 616 and WO 96/31461 describe 2-[2-(alkoxy)phenoxy]ethylamine derivatives of formula:

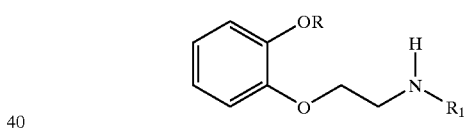

in which R is a $C_1-C_4$ alkyl group and $R_1$ represents a 4-benzenebutyl, piperidine-4-methyl or 4-benzamidobutyl chain. These compounds are claimed as being ligands of the receptors of the 5-$HT_{1A}$ subtype (FR 2 702 211 and WO 96/31461) or hypotensive agents and tranquilizers (JP 51 048 627, JP 51 052 146 and DE 2 450 616). Patent EP 707 007 describes arylamines with twofold activity: both antagonist of the receptors of the $D_2$ type, and agonist of the 5-$HT_{1A}$ subtype, and which are useful as antipsychotic agents. The compound EMD-12830 (Drug Data Report 1998, 21) of formula:

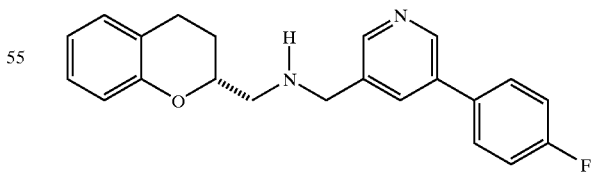

is claimed as an atypical antipsychotic agent (i.e. an agent with a reduced propensity to cause side effects of Parkinson type than the conventional antipsychotic agents).

Patent DE 2 364 685 describes phenoxyalkylamines, in particular N-[2-(2-methoxyphenoxy)ethyl]-3- or -4-pyridylmethanamine, are [sic] claimed as hypotensive agents.

Angstein et al. (J. Med. Chem. 196 5, 8, 356) have described aryloxyalkylamines that are active on the cardiovascular system. Among the compounds described is N-[2-(2-methoxyphenoxy)ethyl]benzenemethanamine.

Goldenberg et al. (Chim. Ther. 1973, 8, 259) have described, inter alia, N-[2-(2-methoxyphenoxy)ethyl-2-benzofuranmethanamines as agents with peripheral vasodilatory properties.

4-Methoxy-3-[2-[(phenylmethyl)amino]ethoxy]phenol is described in J. Labelled Compd. Radiopharm. 1993, 33, 1091 and N-[2-(2-methoxyphenoxy)ethyl]furfurylamine is described in FR 1 336 684.

Patent WO 98/11068 describes 1-(2-pyrimidyl)-4-[(3-aryl)benzyl]piperazines as selective ligands of the receptors of the $D_4$ subtype.

SUMMARY OF THE INVENTION

The present invention relates to a novel family of compounds which correspond to the general formula (1)

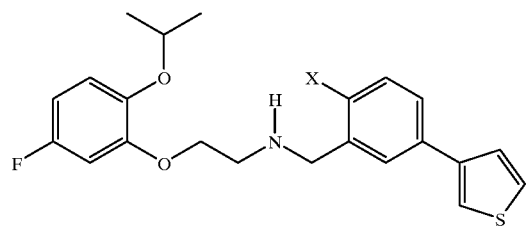

formula 1

The compounds of this invention have antidopaminergic activity, in particular on the receptors of the $D_2$ subfamily. In this respect, the compounds of the invention are useful in the treatment of conditions resulting from dopaminergic hyperactivity, such as schizophrenic symptoms and dependency on certain substances. However, the antagonist activity of the products of the invention on the receptors of the $D_2$ type is exerted only during a transient dopaminergic hyperstimulation. In the absence of dopaminergic hyperactivity, that is to say when the dopamine concentration ranges within proportions that are acceptable for normal functioning of the neuron, the compounds of the invention do not induce dopaminergic hypoactivity. The compounds of the invention are thus useful in the treatment of schizophrenic symptoms and have the advantage of being potentially free of the adverse side effects caused by an excessive blocking of the receptors of the $D_2$ type, such as Parkinsonian symptoms and/or endocrine disorders, at doses that are therapeutically effective for treating schizophrenic psychosis.

The compounds of the invention thus differ from the derivatives of the prior art in their chemical formula and their mechanism of action.

DETAILS OF THE INVENTION

More specifically, the present invention relates to novel compounds corresponding to the general formula (1).

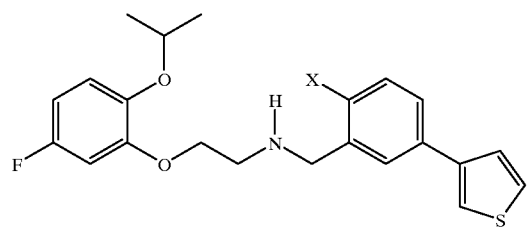

formula 1 in which:
X represents:
  a hydrogen or fluorine atom;
  a hydroxyl (OH) group or a methoxy ($OCH_3$) group.

The invention also relates to the addition salts and optionally the hydrates of the addition salts of the compounds of general formula (1) with pharmaceutically acceptable mineral acids or organic acids.

A subject of the invention is also pharmaceutical compositions containing, as active principle, at least one of the derivatives of general formula (1) or one of the salts thereof or hydrates of the salts thereof in combination with one or more pharmaceutically acceptable excipients, adjuvants or vehicles. By way of example, mention may be made of inclusion complexes, in particular the inclusion complexes formed by the compounds of the invention with □-cyclodextrins.

The pharmaceutical compositions according to the invention may be compositions which may be administered orally, nasally, sublingually, rectally or parenterally. It is generally advantageous to formulate such pharmaceutical compositions in unit dose form. Each dose then comprises a predetermined amount of the active principle, combined with the appropriate vehicle, excipients and/or adjuvants, calculated to obtain a given therapeutic effect. By way of example of unit dose forms which may be administered orally, mention may be made of tablets, gel capsules, granules, powders and oral solutions or suspensions.

The formulations that are appropriate for the chosen administration form are known and described, for example, in: Remington, The Science and Practice of Pharmacy, 19th Edition, 1995, Mack Publishing Company, and may thus be readily prepared by a person skilled in the art.

It is known that the dosage varies from one individual to another, depending on the nature and intensity of the complaint, the chosen route of administration and the weight, age and sex of the patient; consequently, effective doses will have to be determined as a function of these parameters by the specialist in the art. As a guide, the effective doses may range between 0.001 and 100 mg/kg/day.

The compounds of general formula (1) may exist in several tautomeric forms. Such tautomeric forms, although not explicitly reported in the present application to simplify the graphic representation of the structural formulae, are nevertheless included in the field of application of the invention.

The compounds of general formula (1) in which X to [sic] the same meaning as above may be prepared according to the process described in Scheme A.
Scheme A
The compound of formula (1) is prepared by a conventional reductive amination reaction between the compound of formula (2), in which X represents a hydrogen or fluorine atom, a hydroxyl (OH) group or a methoxy ($OCH_3$) group, and the primary amine of formula (3). The expression "a conventional reductive amination reaction" means that the compound of formula (2) and the amine (3) are reacted together in the suitable solvent and that the mixture of the reagents (2) and (3) is then subjected to the reducing agent according to a method that is well known to those skilled in the art.

The compounds of formula (1) are purified according to one or more methods chosen from crystallization and/or liquid phase chromatography techniques. They may then be, if so desired:

salified using a pharmaceutically acceptable acid;

employed in the formation of an inclusion complex.

The primary amine of formula (3) perhaps [sic] obtained by the process described in Scheme B.

Scheme B

4-Fluoro-2-hydroxyacetophenone of formula (4) is converted into the protected amine of formula (5) in two steps:

a Williamson reaction between the compound of formula (4) and 1-bromo-2-chloroethane, carried out in the corresponding chloro ether (J. Med. Chem. 1989, 32, 105);

substitution of the chlorine atom using potassium phthalimide to give the compound of formula (5). A Bayer-Villiger reaction, carried out on the compound of formula (5) according to Synth. Commun 1989, 11/12, 2001, followed by a basic hydrolysis reaction of the intermediate formate, gives the phenol of formula (6). Alkylation of the phenol of formula (6), using 2-iodopropane, gives the intermediate of formula (7).

The primary amine of formula (3), prepared from the compound of formula (7) by aminolysis of the phthalimido group, is used immediately in the following reductive amination step (Scheme A). The deprotection of the primary amine group of the compound of formula (7) is carried out by moderate heating (60° C.) in the presence of an excess of 2-aminoethanol.

The aldehydes of formula (2), in which in which [sic] X to [sic] the same meaning as above, are prepared by the process described in Scheme C.

Scheme C

Coupling of the bromo derivatives of formula (8), which are commercially available, with 3-thiopheneboronic acid, which is commercially available, in the presence of a suitable palladium catalyst according to the Suzuki method gives the aldehydes of formula (2) directly.

Scheme A

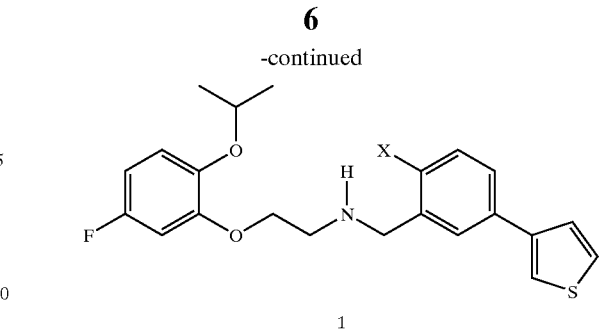

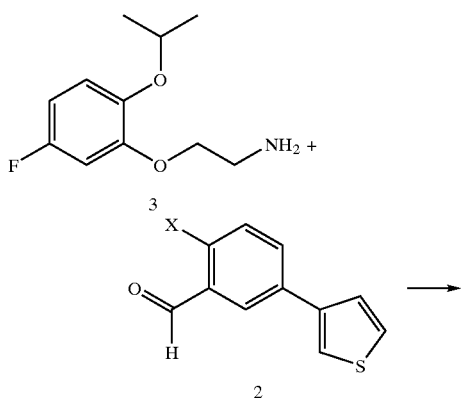

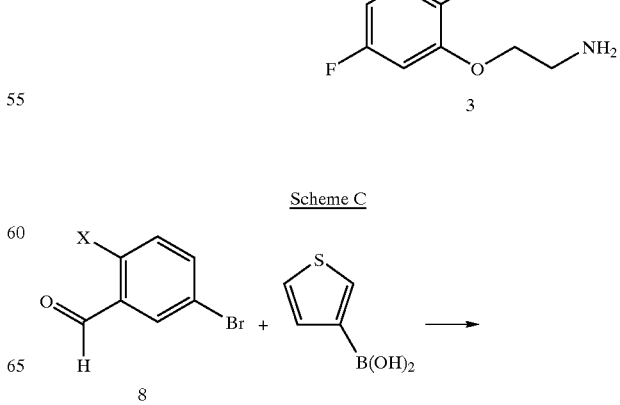

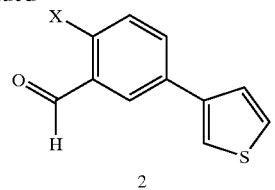

The examples which follow illustrate the invention.

In the examples below:

(i) The reaction progress is monitored by thin layer chromatography (TLC) and, consequently, the reaction times are mentioned merely as a guide.

(ii) Different crystalline forms may give different melting points; the melting points given in the present application are those of the products prepared according to the method described, and are uncorrected.

(iii) The structure of the products obtained according to the invention is confirmed by the nuclear magnetic resonance (NMR) and infrared (IR) spectra and the elemental analysis, and the purity of the final products is checked by TLC.

(iv) The NMR spectra are recorded in the solvent indicated. The chemical shifts (δ) are expressed in parts per million (ppm) relative to tetramethylsilane. The multiplicity of the signals is indicated by: s, singlet; d, doublet; t, triplet; q, quartet; m, multiplet; b, broad.

(v) The various symbols for the units have their usual meaning: mg (milligram); g (gram); ml (milliliter); ° C. (degree Celsius); mmol (millimole); nmol (nanomole); cm (centimeter).

(vi) The abbreviations have the following meanings: m.p. (melting point); b.p. (boiling point).

(vii) In the present application, the pressures are given in millibar; the term "room temperature" means a temperature of between 20° C. and 25° C.

3-(3-Thienyl)benzaldehyde (2a)

3.11 g of 3-thiopheneboronic acid (0.024 mol) are added to a solution of 3-bromobenzaldehyde (3 g, 0.016 mol) in 1,2-dimethoxyethane (80 ml), followed by addition of aqueous 2N sodium carbonate solution (5.15 g, 0.048 mol) and a catalytic amount of tetrakis(triphenylphosphine)palladium (0.56 g, 4.9 $10^{-4}$ mol). The reaction mixture is heated at 80° C. for 16 hours and is then cooled to room temperature and poured into water. The resulting mixture is extracted with ethyl acetate and the organic phase is washed with saturated aqueous sodium chloride solution. The organic phase is dried over magnesium sulfate and filtered, and the solvent is evaporated off under reduced pressure. The title product is isolated by chromatography on a column of silica (eluent: 90/10 cyclohexane/ethyl acetate). 2.61 g of a pale yellow solid are recovered.

Yield: 86% m.p.: 59° C.

1H NMR (CDCl$_3$) δ: 7.46 (s, 2H); 7.53–7.59 (m, 2H); 7.79 (d, J=7.68 Hz, 1H); 7.86 (d, J=8.88 Hz, 1H).

2-Fluoro-5-(3-thienyl)benzaldehyde (2b)

1.89 g of 3-thiopheneboronic acid (0.015 mol) are added to a solution of 3-bromo-6-fluorobenzaldehyde (2 g, 0.016 mol) in 35 ml of 1,2-dimethoxyethane, followed by addition of aqueous 2N sodium carbonate solution (3.13 g, 0.030 mol) and a catalytic amount of tetrakis(triphenylphosphine) palladium (0.34 g, 2.96 $10^{-4}$ mol). The reaction mixture is heated at 80° C. for 20 hours and is then cooled to room temperature and poured into water. The resulting mixture is extracted with ethyl acetate and the organic phase is washed with saturated aqueous sodium chloride solution. The organic phase is dried over magnesium sulfate and filtered, and the solvent is evaporated off under reduced pressure. The title product is isolated from the black oil obtained by bulb-to-bulb distillation at 150° C. under reduced pressure (4 $10^{-2}$ mmbar). 1.36 g of a pale yellow oil which solidifies are isolated.

Yield: 67% m.p.: 71° C.

1H NMR (CDCl$_3$) δ: 7.21 (t, J=9.16 Hz, 1H); 7.36–7.43 (m, 2H); 7.47 (s, 1H); 7.80 (m, 1H); 8.06 (dd, J=6.48; 2.24 Hz, 1H); 10.37 (s, 1H)

2-Hydroxy-5-(3-thienyl)benzaldehyde (2c)

0.15 g of tetrakis(triphenylphosphine)palladium catalyst (1.3 $10^{-4}$ mol) is added to a solution of 5-bromosalicylaldehyde (0.86 g, 0.0043 mol) and of 3-thiopheneboronic acid (0.6 g, 0.0047 mol) in 10 ml of 1,2-dimethoxyethane and 5 ml of methanol. 1.3 g of cesium fluoride are added and the mixture is heated at 80° C. for 20 hours. The reaction mixture is cooled to room temperature and poured into water. The resulting mixture is extracted with dichloromethane and the organic phase is washed with saturated aqueous sodium chloride solution. The organic phase is dried over magnesium sulfate, filtered and concentrated under reduced pressure. The title product is isolated by chromatography on a column of silica (eluent: 88/12 cyclohexane/ethyl acetate). 0.62 g of a pale yellow solid is recovered.

Yield: 71% m.p.: 120° C. 1H NMR (CDCl$_3$) δ: 7.04 (d, J=8.32 Hz, 1H); 7.35 (m, 1H); 7.41 (m, 2H); 7.76 (m, 2H); 9.96 (S, 1H); 11.02 (s, 1H).

2-Methoxy-5-(3-thienyl)benzaldehyde (2d)

3 g of 5-bromo-2-anisaldehyde (0.014 mol) are dissolved in 45 ml of 1,2-dimethoxyethane and 2.68 g of 3-thiopheneboronic acid (0.021 mol) are added, followed by addition of aqueous 2N sodium carbonate solution (4.44 g, 0.042 mol) and a catalytic amount of tetrakis (triphenylphosphine)palladium (0.48 g, 4.19 $10^{-4}$ mol). The reaction mixture is heated at 80° C. for 20 hours with stirring and is then cooled to room temperature and poured into water. The resulting mixture is extracted with ethyl acetate and the organic phase is washed with saturated aqueous sodium chloride solution. The resulting phase is dried over magnesium sulfate and then filtered, and the solvent is evaporated off under reduced pressure. The title product is isolated by chromatography on a column of silica (eluent: 94/6 cyclohexane/ethyl acetate). 2 g of a beige-colored solid are isolated.

Yield: 67% m.p.: 79° C.

1H NMR (CDCl$_3$) δ: 3.97 (s, 3H); 7.02 (d, J=8.80 Hz, 1H); 7.39 (m, 3H); 7.78 (dd, J=8.60; 2.24 Hz, 1H); 8.05 (d, J=2.24 Hz, 1H).

2-[2-(2-Acetyl-5-fluorophenoxy)ethyl]isoindole-1,3-dione (5)

Step 1: 1-[2-(2-chloroethoxy)-4-fluorophenyl]ethanone 40.5 ml of 1-bromo-2-chloroethane (490 mmol) are added at room temperature to a solution of 25 g of 1-[2-hydroxy- 4-fluorophenyl]ethanone (162 mmol) in 2-butanone (400 ml), followed by addition of 45 g of potassium carbonate (320 mmol) and 1.26 g of potassium iodide (7.59 mmol).

The mixture is heated at 80° C. with vigorous stirring for 60 hours and is then cooled to room temperature and poured into ice-cold water. The resulting mixture is extracted with ethyl acetate and the organic phase is washed with saturated aqueous sodium chloride solution. The organic phase is then dried over magnesium sulfate and filtered, and the solvent is evaporated off. The product is crystallized from a cyclohexane/ethyl acetate mixture. 15.7 g of a white solid are recovered.

Yield: 45% m.p.: 67° C.

1H NMR (CDCl$_3$) δ: 2.66 (s, 3H); 3.91 (t, 2H); 4.32 (t, 2H); 6.62 (dd, 1H); 6.76 (dt, 1H); 7.85 (dt, 1H).

Step 2: 2-[2-(2-acetyl-5-fluorophenoxy)ethyl]
isoindole-1,3-dione (5)

A mixture of 14.6 g of potassium phthalimide (79 mmol) and 15 g of 1-[2-(2-chloroethoxy)-4-fluorophenyl]ethanone (69.2 mmol) in 150 ml of N,N-dimethyl-formamide is heated at 150° C. for 6 hours. The mixture is then cooled and the solvent is evaporated off under vacuum. The solid obtained is taken up in dichloromethane and the organic phase is washed with water and then with saturated aqueous sodium chloride solution. The organic phase is then dried over magnesium sulfate and filtered, and the solvent is evaporated off. The product obtained is purified by crystallization from a cyclohexane/ethyl acetate mixture. 18.2 g of a white solid are obtained.

Yield: 76% m.p.: 140° C.

1H NMR (CDCl$_3$) δ: 2.55 (s, 3H); 4.19 (t, 2H); 4.34 (t, 2H); 6.67 (m, 2H); 6.69 (m, 1H); 7.77 (m, 2H); 7.80 (m, 2H).

IR (KBr) □: 1774, 1716, 1679. 1605 and 1590.

2-[2-(5-Fluoro-2-hydroxyphenoxy)ethyl]isoindole-1,
3-dione (6)

A solution of 26 g of meta-chloroperbenzoic acid (at 55%, 82.9 mmol) in 220 ml of dichloromethane is stirred for one hour and then transferred into a separating funnel. The aqueous phase is separated out and the organic phase is placed in a round-bottomed flask and cooled to 0° C. 18 9 of 2-[2-(2-acetyl-5-fluoro-phenoxy)ethyl]isoindole-1,3-dione (5) (55 mmol) are added portionwise and the mixture is stirred at room temperature for 16 hours. 6.9 g of sodium bicarbonate (82 mmol) are then introduced portionwise and the mixture is stirred for one hour. The mixture is then concentrated under vacuum and 200 ml of methanol are added, followed by addition of 15.2 g of potassium carbonate (110 mmol). The mixture is stirred for 4 hours at room temperature and the solvent is then evaporated off, replaced with 200 ml of dichloromethane and the mixture is washed with water and with saturated aqueous sodium chloride solution. The aqueous phase is dried over sodium sulfate and filtered, and the solvent is evaporated off. The product is crystallized from dichloromethane. 14 g of the title product are obtained in the form of a white solid.

Yield: 84% m.p.: 172° C.

1H NMR (DMSO d$_6$) δ: 3.95 (t, 2H); 4.22 (t, 2H); 6.58 (dt, 1H); 6.75 (t, 1H); 6.85 (m, 1H); 7.64 (m, 4H); 8.77 (s, 1H (exchangeable)).

2-[2-(5-Fluoro-2-isopropoxyphenoxy)ethyl]
isoindole-1,3-dione (7)

7.71 g of potassium carbonate (56 mmol) and 7 ml of 2-iodopropane (70 mmol) are added to a solution of 14 g of 2-[2-(5-fluoro-2-hydroxyphenoxy)ethyl]isoindole-1,3-dione (6) (47 mmol) in 250 ml of acetonitrile. The mixture is stirred for 16 hours at 80° C. and the solvent is then evaporated off under reduced pressure and the residue is taken up in diethyl ether. The organic phase is washed with normal aqueous sodium hydroxide solution and then with saturated aqueous sodium chloride solution. It is dried over magnesium sulfate and filtered, and the solvent is evaporated off under vacuum. The title product is isolated by chromatography on a column of silica (eluent: 82/18 cyclohexane/ethyl acetate). 12.2 g of a white solid are isolated.

Yield: 77% m.p.: 68° C.

1H NMR (CDCl$_3$) δ: 1.20 (s, 3H); 1.21 (s, 3H); 4.14 (t, J=5.20 Hz, 2H); 4.23 (t, J=5.20 Hz, 2H); 4.30 (sept, J=6.00 Hz; 1H); 6.56 (dt, 1H); 6.65 (dd, 1H); 6.79 (dd, 1H); 7.73 (m, 2H); 7.86 (m, 2H).

2-(5-Fluoro-2-isopropoxy)phenoxyethylamine (3)

5 g of 2-[2-(5-fluoro-2-isopropoxyphenoxy)ethyl] isoindole-1,3-dione (7) (14.6 mmol) are added to 20 ml of ethanolamine and the solution is then maintained at 60° C. for 2 hours. The mixture is poured into ice-cold water and then extracted with ethyl acetate. The organic phase is washed with saturated aqueous sodium chloride solution, dried over sodium sulfate and filtered, and the solvent is evaporated off under vacuum. 2.54 g of the title product are obtained in the form of a pale yellow oil, which is used directly in the following step without further purification.

Yield: 81%

1H NMR (CDCl$_3$) δ: 1.31 (s, 3H); 1.32 (s, 3H); 1.46 (brs, 2H); 3.09 (t, J=5.20 Hz, 2H); 3.99 (t, J=5.20 Hz, 2H); 4.35 (sept, J=6.00 Hz, 1H); 6.60 (dt, J=8.32; 3.00 Hz 1H); 6.64 (dd, J=10.16; 2.92 Hz, 1H); 6.84 (dd, J=8.80; 5.76 Hz, 1H).

[3-(3-Thienyl)benzyl]-[2-([5-fluoro-2-isopropoxy]-
phenoxy)ethyl]amine (1a)

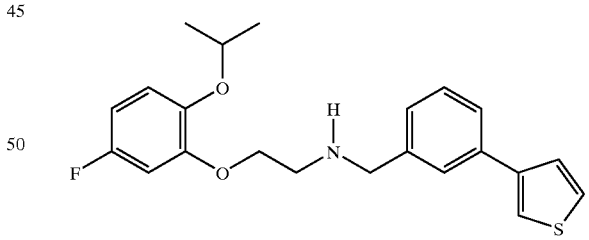

2.5 g of magnesium sulfate are added to a solution of 3-(3-thienyl)benzaldehyde (2a) (700 mg, 3.72 mmol) and of 2-(5-fluoro-2-isopropoxy)phenoxyethylamine (3) (793 mg, 3.72 mmol) in 15 ml of 1,2-dichloroethane, and the mixture is heated at 60° C. for 17 hours with stirring. The reaction is then cooled to room temperature, the solid is filtered off and the solvent is evaporated off under reduced pressure. 15 ml of methanol are then added to the residue and the resulting mixture is cooled to 0° C. 400 mg of potassium borohydride (7.44 mmol) are introduced and the mixture is stirred for three hours at 0° C. The mixture is then poured into ice-cold water and extracted with ethyl acetate, and the organic phase is washed with saturated aqueous sodium chloride solution. The resulting phase is dried over magnesium sulfate and then filtered, and the solvent is evaporated off under reduced pressure. The title product is obtained by chromatography on a column of silica (eluent: 98/1.5/0.5 dichloromethane/methanol/aqueous ammonia). 970 mg of a colorless oil are isolated.

Yield: 68%

Preparation of the salt: 0.97 g of the title product (2.52 mmol) is dissolved in 10 ml of ethanol and 0.23 g of oxalic acid (2.52 mmol) in 10 ml of ethanol is then added. The solution is concentrated, the salt precipitates, and the concentrated solution is filtered. The salt is dried under vacuum at 50° C. 0.96 g of the title compound is obtained in the form of the oxalate salt, a white crystalline powder.

m.p.: 189° C.

Analysis $C_{24}H_{26}FNO_6S$

Calc %: C, 60.62; H, 5.51; N, 2.95; S, 6.74.

Found: 60.59; 5.72; 2.99; 6.57.

1H NMR (DMSO $d_6$) δ: 1.21 (s, 6H); 3.31 (t, J=4.80 Hz, 2H); 4.32 (m, 4H); 4.48 (sept, J=6.00 Hz, 1H); 6.73 (m, 1H); 6.99 (m, 2H); 7.28 (m, 2H); 7.55 (d, J=4.84 Hz, 1H); 7.66 (d, J=7.04 Hz, 1H); 7.75 (d, J=7.20 Hz, 1H); 7.88 (d, J=9.24 Hz, 2H).

IR (KBr) ☐: 3436; 2979; 1718 cm$^{-1}$.

[2-Fluoro-5-(3-thienyl)benzyl]-[2-([5-fluoro-2-isopropoxy]phenoxy)ethyl]amine (1b)

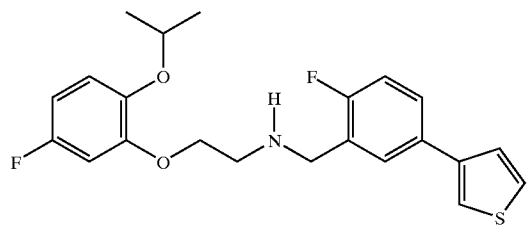

A solution of 2-fluoro-3-(3-thienyl)benzaldehyde (2b) (350 mg, 1.64 mmol) and of 2-(5-fluoro-2-isopropoxy)phenoxyethylamine (3) (338 mg, 1.64 mmol) in 15 ml of toluene is heated at 130° C. for 17 hours in a 50 ml round-bottomed flask equipped with Dean-Stark apparatus. The reaction is then cooled to room temperature, the solvent is evaporated off under reduced pressure and the residue is dissolved in 15 ml of methanol. The reaction mixture is cooled to 0° C. and 177 mg of potassium borohydride (3.28 mmol) are added. The mixture is stirred for seven hours at room temperature and is then poured into ice-cold water and extracted with ethyl acetate, and the organic phase is washed with saturated aqueous sodium chloride solution. The resulting phase is dried over magnesium sulfate and filtered, and the solvent is evaporated off under reduced pressure. The title product is isolated by chromatography on a column of silica (eluent: 98/1.5/0.5 dichloromethane/methanol/aqueous ammonia) to give 436 mg of a yellow oil.

Yield: 66%

Preparation of the salt: 427 mg of the title product (1.06 mmol) are dissolved in 10 ml of methanol, followed by addition of 95 mg of oxalic acid (1.06 mmol) in 5 ml of ethanol. The solution is concentrated, the salt precipitates and the concentrated solution is filtered. The salt is dried under vacuum at 50° C. 417 mg of the title compound are obtained in the form of the oxalate salt, a white crystalline powder.

m.p.: 173° C.

Analysis $C_{24}H_{25}F_2NO_6S$

Calc %: C, 58.41; H, 5.11; N, 2.84.

Found: 58.62 5.13 2.86.

1H NMR (DMSO $d_6$) δ: 1.18 (s, 3H); 1.19 (s, 3H); 3.33 (t, J=4.80 Hz, 2H); 4.27 (t, J=4.80 Hz, 2H); 4.31 (s, 2H); 4.45 (sept, J=6.00 Hz, 1H); 6.74 (dt, J=8.50; 2.88 Hz, 1H); 7.00 (m, 2H); 7.32 (t, J=9.36 Hz, 1H); 7.52 (d, J=5.00 Hz, 1H); 7.66 (m, 1H); 7.77 (m, 1H); 7.83 (d, J=1.84 Hz, 1H); 7.85 (dd, J=7.00; 1.92 Hz, 1H).

IR (KBr) : 3045; 2848; 1719 cm$^{-1}$.

[2-Hydroxy-5-(3-thienyl)benzyl][2-([5-fluoro-2-isopropoxy]phenoxy)ethyl]amine (1c)

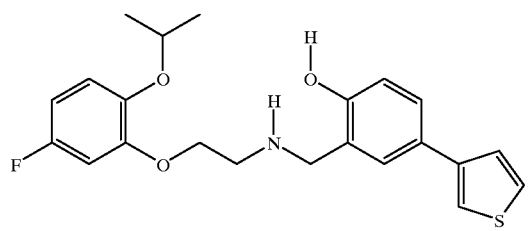

A solution of 2-hydroxy-3-(3-thienyl)benzaldehyde (2c) (400 mg, 1.96 mmol) and of 2-(5-fluoro-2-isopropoxy)phenoxyethylamine (3) (418 mg, 1.96 mmol) in 20 ml of toluene is heated at 130° C. for 20 hours with stirring, with continuous removal of the water formed using Dean-Stark apparatus. The reaction is then cooled to room temperature, the orange-colored solution is concentrated under reduced pressure and the residue is dissolved in 10 ml of methanol. The reaction mixture is cooled to 0° C. and 211 mg of potassium borohydride (3.92 mmol) are introduced. The mixture is stirred for three hours at room temperature and is then poured into ice-cold water and extracted with dichloromethane, and the organic phase is washed with saturated aqueous sodium chloride solution. The resulting phase is dried over sodium sulfate and filtered, and the solvent is evaporated off under reduced pressure. The title product is isolated by chromatography on a column of silica (eluent: 98/1.5/0.5 dichloro-methane/methanol/aqueous ammonia) to give 526 mg of a yellow solid.

Yield: 67% m.p.: 75° C.

Preparation of the salt: 468 mg of the title product (1.17 mmol) are dissolved in 10 ml of ethanol, followed by addition of 105 mg of oxalic acid (1.17 mmol) in 5 ml of ethanol. The solution is concentrated, the salt precipitates and the concentrated solution is filtered. The salt is dried under vacuum at 50° C. 496 mg of the title compound are obtained in the form of the oxalate salt, a white crystalline powder.

m.p.: 205° C.

Analysis $C_{24}H_{26}FNO_7S$

Calc %: C, 58.65; H, 5.33; N, 2.85.

Found: 58.81; 5.50; 2.97.

1H NMR (DMSO $d_6$) δ: 1.19 (s, 3H); 1.21 (s, 3H); 3.32 (t, J=4.80 Hz, 2H); 4.29 (m, 4H); 4.47 (sept, J=6.00 Hz, 1H); 6.75 (dt, J=8.48; 2.76 Hz, 1H); 6.95–7.02 (m, 3H); 7.44 (d, J=4.96 Hz, 1H); 7.57–7.72 (m, 3H); 7.83 (s, 1H).

IR (KBr) ☐: 3450, 3156, 2989, 1733 cm$^{-1}$.

[2-Methoxy-5-(3-thienyl)benzyl][2-([5-fluoro-2-isopropoxy]phenoxy)ethyl]amine (1d)

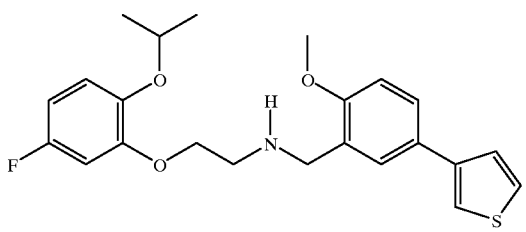

1.5 g of magnesium sulfate are added to a solution of 2-methoxy-3-(3-thienyl)benzaldehyde (2d) (510 mg, 2.34 mmol) and of 2-(5-fluoro-2-isopropoxy)phenoxyethylamine (3) (500 mg; 2.34 mmol) in 10 ml of 1,2-dichloroethane, and the mixture is heated at 60° C. for 20 hours with stirring. The reaction is cooled to room temperature, the solid is filtered off and the solvent is evaporated off under reduced pressure. The residue is dissolved in 11 ml of methanol and the resulting solution is cooled to 0° C. 252 mg of potassium borohydride (4.68 mmol) are added and the mixture is stirred for 16 hours at room temperature. The mixture is then poured into ice-cold water and extracted with ethyl acetate, and the organic phase is washed with saturated aqueous sodium chloride solution. The resulting phase is dried over sodium sulfate and then filtered, and the solvent is evaporated off under reduced pressure. The title product is obtained by chromatography on a column of silica (eluent: 80/20 cyclohexane/ethyl acetate). 307 mg of a colorless oil are isolated.

Yield: 32%

Preparation of the salt: 298 mg of the title product (7.17 mmol) are dissolved in 8 ml of ethanol followed by addition of 65 mg of oxalic acid (7.17 mmol) in 5 ml of ethanol. The solution is concentrated, the salt precipitates and the concentrated solution is filtered. The salt is dried under vacuum at 50° C. 245 mg of the title compound are obtained in the form of the oxalate salt, a white crystalline powder.

m.p.: 157° C.

Analysis $C_{25}H_{28}FNO_7S$

Calc %: C, 59.39; H, 5.58; N, 2.77.

Found: 59.85; 5.79; 3.05.

1H NMR (DMSO $d_6$) δ: 1.18 (s, 3H); 1.20 (s, 3H); 3.26 (t, J=4.80 Hz, 2H); 3.84 (s, 3H); 4.21 (s, 2H); 4.25 (t, J=4.80 Hz, 2H); 4.45 (sept, J=6.00 Hz, 1H); 6.75 (dt, J=8.52; 2.92 Hz, 1H); 6.99 (m, 2H); 7.11 (d, J=8.60 Hz, 1H); 7.49 (d, J=5.00 Hz, 1H); 7.63 (m, 1H); 7.71–7.94 (m, 3H).

IR (KBr) □: 2977, 1610 cm$^{-1}$.

Pharmacological study of the compounds of the invention

1—Measurement of the affinity of the compounds of the invention for the $D_2$ receptors.

The affinity of the compounds of the invention for the receptors of the $D_2$ type was determined by measuring the displacement of ($^3$H) YM-09151-2 (NET-1004 70–87 Ci/mmol), according to the method described in Naunyn-Schimiedeberg's Arch. Pharmacol. Methods, 1985, 329, 333. The pKi values (–log Ki) are given in the form of a mean ±SEM of at least 3 experiments.

Table 1 gives, by way of example, the pKi values ($D_2$) for compound 1a and Risperidone.

2—Evaluation of the antagonist activity of the $D_2$ receptors and of the cataleptogenic effects of the compounds of the invention in vivo The test demonstrating the antidopaminergic activity in vivo of the compounds of the invention is based on the inhibition of the behavior induced by methylphenidate, measured in rats, according to the method described in J. Pharmacol. Exp. Ther. 1993, 267, 181.

The test for evaluating the propensity of the products of the invention to cause side effects of extrapyramidal order is based on their cataleptogenic power, measured in rats, according to the method described in Eur. J. Pharmacol. 1996, 313, 25.

By way of example, the values obtained after oral administration of compound 1a are indicated in Table 1 in comparison with the reference substance: Risperidone.

TABLE 1

| Compound | $D_2$ pKi | Normalization $ED_{50}$ mg/kg | Catalepsy $ED_{50}$ mg/kg | Therapeutic Index |
|---|---|---|---|---|
| 1a | 9.45 | 0.7 | >40 | >57 |
| Risperidone | 8.70 | 6.5 | 3.5 | 0.5 |

It emerges from this study that the compounds of the invention have high affinity for the receptors of the $D_2$ type and also powerful antidopaminergic activity in vivo. However, surprisingly, the compounds of the invention do not induce, or induce only at very high doses, cataleptogenic effects, when compared with Risperidone. Risperidone is an atypical antipsychotic agent used clinically (Inpharma® 1998, 1156, 5).

In this respect, the compounds of the invention which are capable of modifying the effects of endogenous dopamine are useful in the treatment of dopaminergic disorders such as schizophrenia, certain neurodegenerative diseases and dependancy on cocaine, alcohol or similar substances.

What is claimed is:

1. A compound of formula (1)

formula 1

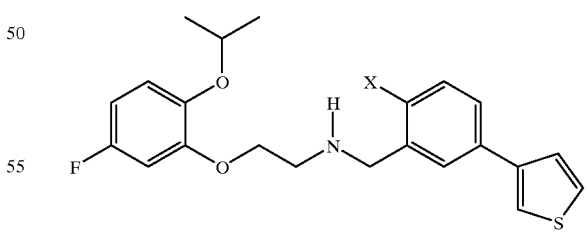

in which:

X represents:
  a hydrogen or fluorine atom;
  a hydroxyl (OH) group or a methoxy (OCH$_3$) group,
and the pharmaceutically acceptable addition salts thereof.

2. The compound of formula (1) as claimed in claim 1, which is selected from:

[3-(3-thienyl)benzyl]-[2-([2-isopropoxy-5-fluoro]-phenoxy)ethyl]amine
[2-hydroxy-5-(3-thienyl)benzyl]-[2-([2-isopropoxy-5-fluoro]phenoxy)ethyl]amine
[2-methoxy-5-(3-thienyl)benzyl]-[2-([2-isopropoxy-5-fluoro]phenoxy)ethyl]amine, and
[2-fluoro-5-(3-thienyl)benzyl]-[2-([2-isopropoxy-5-fluoro]phenoxy)ethyl]amine.

3. A pharmaceutical composition, comprising at least one compound of claim 1 and one or more pharmaceutically acceptable excipient or vehicle.

4. A method for treating a living animal body afflicted with schizophrenia, comprising the step of administering to the body an amount of a compound of claim 1 effective to alleviate the condition.

5. A method for treating a living animal body afflicted with dependency on cocaine or alcohol, comprising the step of administering to the body an amount of a compound of claim 1 effective to alleviate the condition.

6. A method for treating a living animal body afflicted with neurodegenerative diseases, comprising the step of administering to the body an amount of a compound of claim 1 effective to alleviate the condition.

\* \* \* \* \*

UNITED STATES PATENT AND TRADEMARK OFFICE
CERTIFICATE OF CORRECTION

PATENT NO.    : 6,417,222 B1                                             Page 1 of 1
DATED         : July 9, 2002
INVENTOR(S)   : Bernard Vacher et al.

It is certified that error appears in the above-identified patent and that said Letters Patent is hereby corrected as shown below:

<u>Title page,</u>
Item [54], Title,
"[2-SUBSTITUTED-5-[3-THIENYL)-BENZYL]-2-([2-ISOPROPOXY-5-FLUORO]-PHENYOXY)-ETHYL]-AMINE DERIVATIVES, METHOD FOR THE PRODUCTION AND USE THEREOF AS MEDICAMENTS"
should be
-- [(2-SUBSTITUTED-5-[3-THIENYL])-BENZYL]-[2-([2-ISOPROPOXY-5-FLUORO]-PHENYOXY)-ETHYL]-AMINE DERIVATIVES, METHOD FOR THE PRODUCTION AND USE THEREOF AS MEDICAMENTS --

Signed and Sealed this

Twenty-sixth Day of November, 2002

*Attest:*

*Attesting Officer*

JAMES E. ROGAN
*Director of the United States Patent and Trademark Office*